United States Patent [19]

Dybel et al.

[11] 4,327,591
[45] May 4, 1982

[54] STRAIN SENSING DEVICE WITH MAGNETIC MOUNTING

[75] Inventors: Frank R. Dybel, Olympia Fields; Kenneth MacDonald, Deerfield, both of Ill.

[73] Assignee: International Measurement & Control Co., Frankfort, Ill.

[21] Appl. No.: 145,223

[22] Filed: Apr. 30, 1980

[51] Int. Cl.³ .............................................. G01L 1/16
[52] U.S. Cl. .................................... 73/855; 73/862.06
[58] Field of Search .................... 73/855, 811, 862.06, 73/862.56, 862.62, 862.38, 862.39, 862.54

[56] References Cited

U.S. PATENT DOCUMENTS 4,010,679 3/1977 Dybel ..................................... 73/811

*Primary Examiner*—Anthony V. Ciarlante
*Attorney, Agent, or Firm*—Leydig, Voit, Osann, Mayer & Holt, Ltd.

[57] ABSTRACT

A magnetically mountable device for sensing deformation from loadings on machine members. The device includes a strain sensing transducer, brackets between which the transducer is supported, and magnetic bracket mounts which permit the transducer to be easily mounted on the machine member by virtue of magnetic attraction forces between the mounts and the force carrying member and yet be readily repositionable on the member so as to facilitate location of points of maximum stress concentrations during a working cycle of the machine.

13 Claims, 5 Drawing Figures

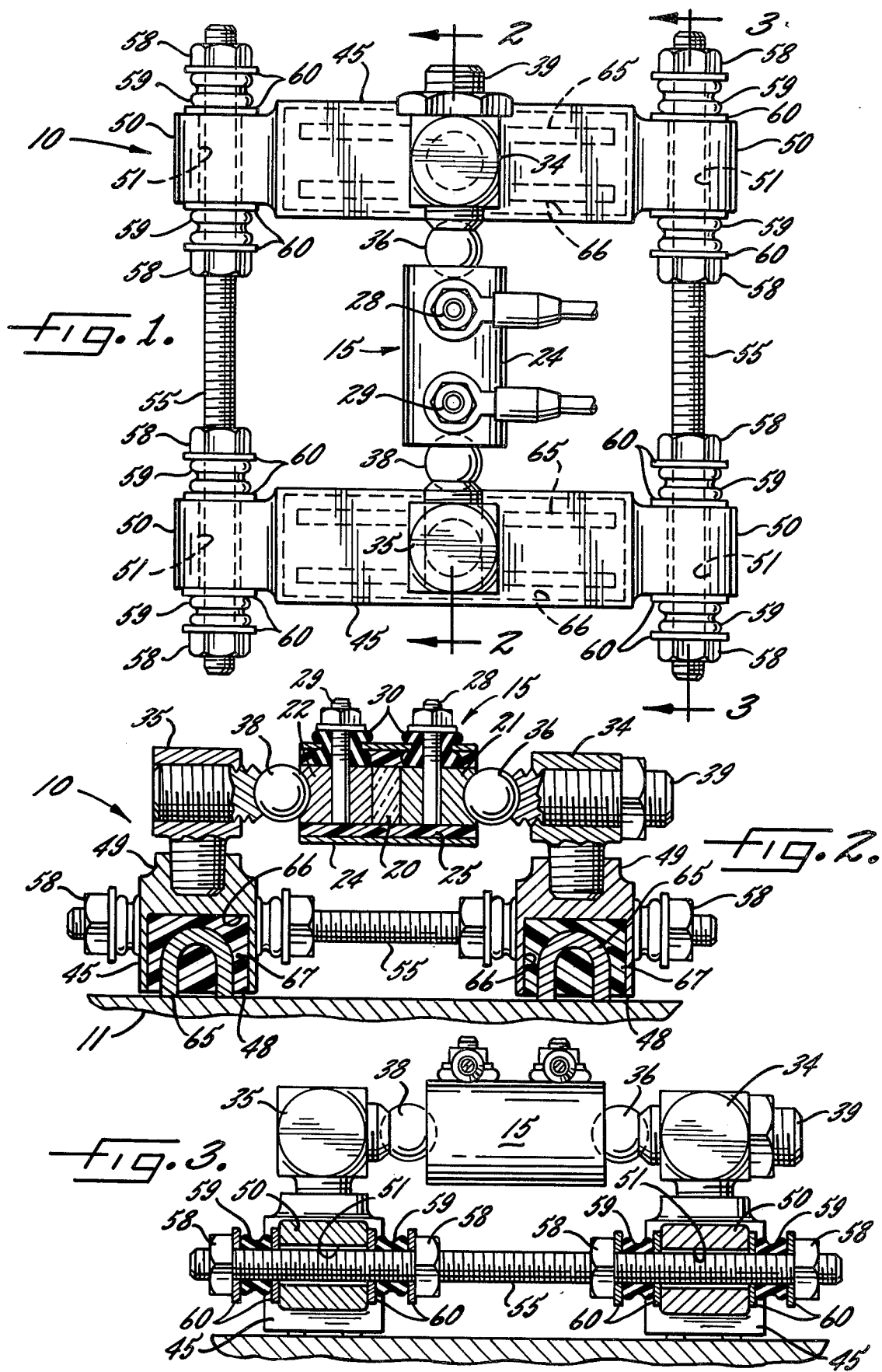

STRAIN SENSING DEVICE WITH MAGNETIC MOUNTING

DESCRIPTION OF THE INVENTION

The present invention relates generally to load monitoring systems, and more particularly to strain sensing transducers for use with such systems.

Various types of transducers are known for sensing the deformation of structural machine members, such as the pitmans of production presses, and providing electrical indications for use with load indicating or control circuitry. Piezioelectric transducers, such as shown in applicant's U.S. Pat. No. 4,010,679, have been found particularly suited for such purpose. In a typical installation, the transducer is mounted between support brackets that are permanently secured to the machine member, such as by threadable engagement with mounting holes that are drilled and tapped into the machine member. In other types of transducers, such as those which employ strain-gage sensing elements, the transducers also are permanently mounted on the machine, either by bolting mounting plates or by adhesively applying the strain gages directly to the machine such that any removal causes their destruction.

Because more versatile and accurate load monitoring systems for punch presses have been developed in recent years, many firms are not familiar with either the installation or operation of such monitoring systems. Moreover, with the development of such monitoring systems, applications on additional types of production equipment are continually being found. As a result, in promoting the sale of such systems, particularly to those not otherwise familiar with such systems, it is highly desirable to be able to demonstrate the system on the actual machine upon which its use is contemplated. Since the strain sensing transducers usually are permanently mountable on the machine—either requiring alteration of the press or destruction of the transducer if it is to be removed—it heretofore has not been possible to effectively demonstrate the operation of such systems to prospective customers or users.

Furthermore, in many machines on which the use of such load monitoring systems are contemplated, it is difficult to determine specific locations on the force carrying members that would best be suited for mounting of the transducers. Again, this is particularly the case when the machine is of a type that has not commonly been equiped with such systems. Difficulties in properly locating the transducer also occur on machines that are exposed to various levels of stress during a work cycle of operation such that the transducer must be precisely located at points where maximum stresses occur.

It is an object of the present invention to provide a load sensing device that is readily and removably mountable on the force carrying member of a machine for the purpose of enabling convenient demonstration of load monitoring systems.

Another object is to provide a strain sensing device as characterized above that is easily repositionable at various locations on the force carrying members for facilitating location of points on the structural member that are exposed to maximum stress concentrations prior to permanent mounting of the transducers.

A further object is to provide a strain sensing device of the foregoing type that is relatively simple in construction and use.

Other objects and advantages of the invention will become apparent upon reading the following detailed description and upon reference to the drawings in which:

FIG. 1 is a plan view of a strain sensing device embodying the present invention;

FIG. 2 is a vertical section taken in the plane of line 2—2 in FIG. 1;

FIG. 3 is a vertical section taken in the plane of line 3—3 in FIG. 1;

Figure 4:
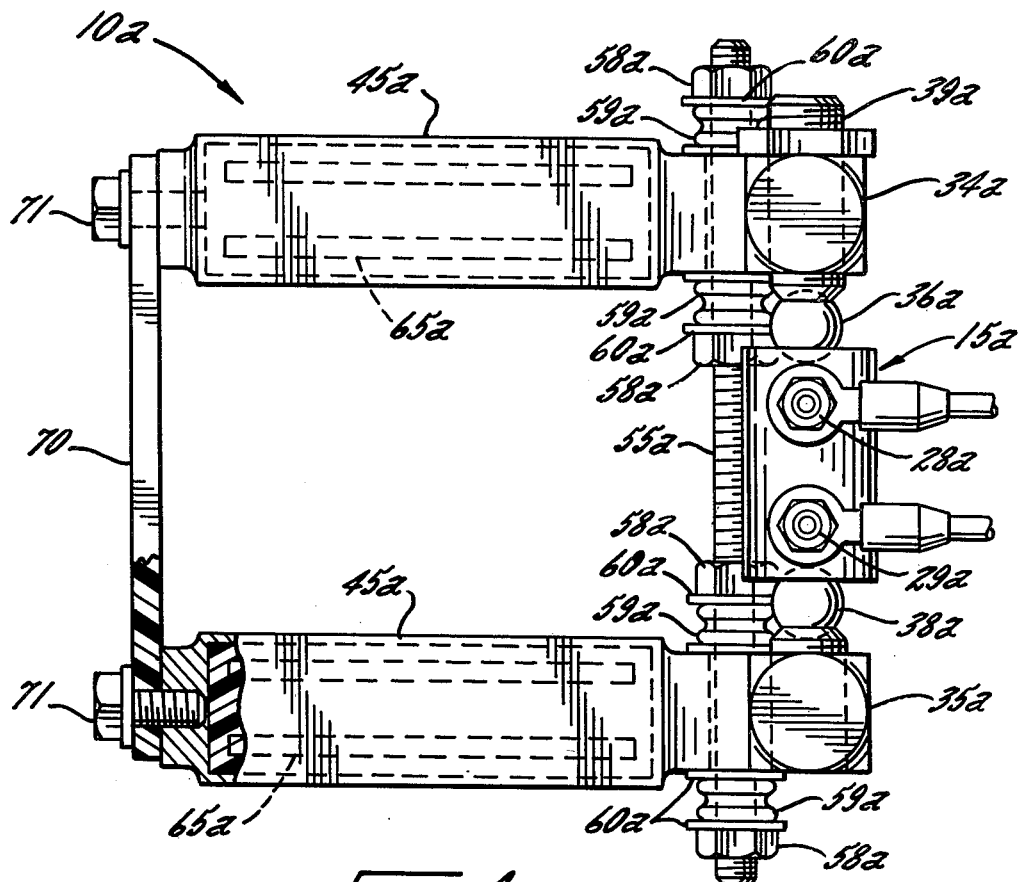
FIG. 4 is a plan view of an alternative embodiment of such a strain sensing device.

While the invention is susceptible of various modifications and alternative constructions, a certain illustrated embodiment thereof has been shown in the drawings and will be described below in detail. It should be understood, however, that there is no intention to limit the invention to the specific form disclosed, but on the contrary, the intention is to cover all modifications, alternative constructions and equivalents falling within the spirit and scope of the invention.

Referring more particularly to the drawings, there is shown an illustrative device 10 embodying the present invention for sensing loads that are intermittently incurred by a force carrying member 11, such as the pitman of a punch press The device 10 includes a transducer 15 having a piezoelectric crystal 20 positioned between terminal blocks 21, 22 with the opposed faces of the crystal 20 being in contact with the respective terminal blocks. The terminal blocks 21, 22 and crystal 20 in this case are surrounded by a metallic sheath 24 which serves as a magnetic and electric shield. The sheath 24 is slightly larger than the terminal blocks and crystal to provide for a surrounding layer 25 of an encapsulating and insulating plastic material. Leading from the terminal blocks through the insulating layer 25 and the metallic sheath 24 are terminals 28, 29 with suitable connections for attachment of leads of an appropriate load monitoring circuit, such as, for example, circuits of the type shown in the applicant FranK R. Dybel U.S. Pat. Nos. 3,612,966 and 3,884,068. The terminals 28, 29, and hence the terminal blocks, are electrically insulated from the sheath 24 at the passageway therethrough by terminal insulators 30. The sheath 24 preferably is grounded to shielded cables that may be utilized for coupling the transducer terminals to the monitoring circuitry.

The transducer 15 in this case is supported between the ends of brackets 34, 35 by means of ball and socket joints, including balls 36, 38 that engage sockets in the terminal blocks 21, 22 respectively. The brackets are electrically insulated from the terminal blocks by the balls 36, 38, which may be made of a refractory insulating material. For permitting selective pre-stressing of the transducer crystal 20, a set screw 39 is provided in the end of the bracket 34.

In accordance with the invention, means are provided for permitting selective and removable mounting of the transducer at various positions on a force carrying member so as to facilitate demonstration of a load monitoring system, temporary installation of the system, or the location of precise points on the machine where maximum strain occurs during a loading cycle.

To this end, in the illustrated embodiment, the transducer support brackets 34, 35 are mounted in respective mounting blocks 45 each having a flat bottom mounting surface 48 that are positionable on any substantially flat surface of a machine member, the loading of which it is desired to monitor. The mounting blocks 45, which are preferably cast of zinc or aluminum, in this instance have an elongated shape and are disposed in spaced parallel relation with the transducer 15 extending between and transversely of the mounting blocks. For carrying the transducer support brackets, the mounting blocks each are formed with a central upper boss 49 which are drilled and tapped for receiving a respective one of the threaded support brackets 34, 35.

For coupling the mounting blocks 45 together while permitting limited relative movement in a direction parallel to the axis of the transducer 15, the mounting blocks are formed with lugs 50 at their opposed ends. The mounting block lugs 50 on each side of the transducer have correspondingly aligned bores 51 for receiving a threaded connecting rod 55, preferably made of aluminum, which extends between the mounting blocks and through the aligned bores 51. The bores 51 are slightly larger in diameter than the rod 55 so as to permit relative movement of the mounting blocks on the rods.

For maintaining the mounting blocks on the rods, while permitting limited relative movement, a pair of nuts 58 threadably engage the rod 55 on each side of the mounting block lugs 50, with flexible spacers 59, such a rubber spacer, being interposed between a respective nut 58 and side of the mounting block. In the present instance, metal washers 60 are disposed on opposite sides of each flexible spacer 59.

In keeping with the invention, the mounting blocks each include a magnetic element that is adapted to permit secure mounting of the blocks and the transducer carried thereby on a metal machine member as an incident to positioning of the device on the machine. In the illustrated embodiment, the mounting blocks 45 each include an elongated magnet 65 contained within a rectangular recessed area 66 of the mounting block which is filled with an insulating plastic material 67 that encloses the top and sides of the magnet. The magnets 65 have a power sufficient to hold the mounting blocks in place on the machine member and enable strain deformation in the member to be transmitted through the mounting blocks 45 and associated brackets 34, 35 to the transducer, while permitting the device to be manually removed and/or repositioned on the force carrying member when desired. In practice, magnets having holding powers of between 40 and 50 pounds each have been found to permit easy and reliable use of the sensing device 10.

In use, it will be seen that the strain sensing device 10 may be readily mounted on any substantially flat metal machine member by merely positioning the underside surfaces of the mounting blocks 45 on the member with the transducer 15 oriented in a direction parallel to the forces to be detected or monitored. With the mounting blocks positioned on the machine member, the magnetic attraction holds the mounting blocks in position. Changes in deformation of the machine member thereafter occuring during operation of the machine are transmitted through the mounting blocks 45 and associated brackets 34, 35 to the transducer 15, which will produce an electrical signal substantially proportional to the loading. It will be appreciated that the flexible spacers 59 permit the relatively minute movement of the mounting blocks with respect to each other and the connecting rods 55 associated with strain deformation of the member, and thus permit the transmission of forces from the mounting blocks and brackets to the transducer.

The strain sensing device of the present invention has enabled the use of load monitoring systems in a number of important ways that have not heretofore been possible. First, because the strain sensing transducer is easily and removably mountable on the force carrying member, the strain sensing device can be readily used for demonstrating various types of load monitoring systems on the actual machines upon which their use is contemplated. The load sensing device need merely be positioned on the force carrying member of the machine, an appropriate load indicator or controller coupled to the output terminals of the transducer, and the machine operated. Moreover, because the strain sensing device is easily removable and respositionable on the machine, it can be placed at various locations on the machine so as to locate precise points on the force carrying members that are exposed to maximum stress concentrations during a working cycle. This is particularly desirable when the machine is exposed to continual stresses or various degrees of stresses, and it is necessary to mount strain sensing transducers at locations where maximum strains are incurred if reliable load monitoring is to be achieved. Finally, the strain sensing device may simply be used for temporarily installing a load monitoring system, such as might be necessary pending receipt of a system for permanent installation on the machine.

It will be understood by one skilled in the art that the surface of the machine member upon which the magnetic mounting blocks are placed should be cleaned of any grease, dirt or other substance which could effect the magnetic holding forces between the mounting blocks and the machine member. In instances where the machine surface is rough or heavily coated with paint, it may be necessary to utilize magnets of greater power in order to insure reliable mounting and force transmission.

Figure 5:
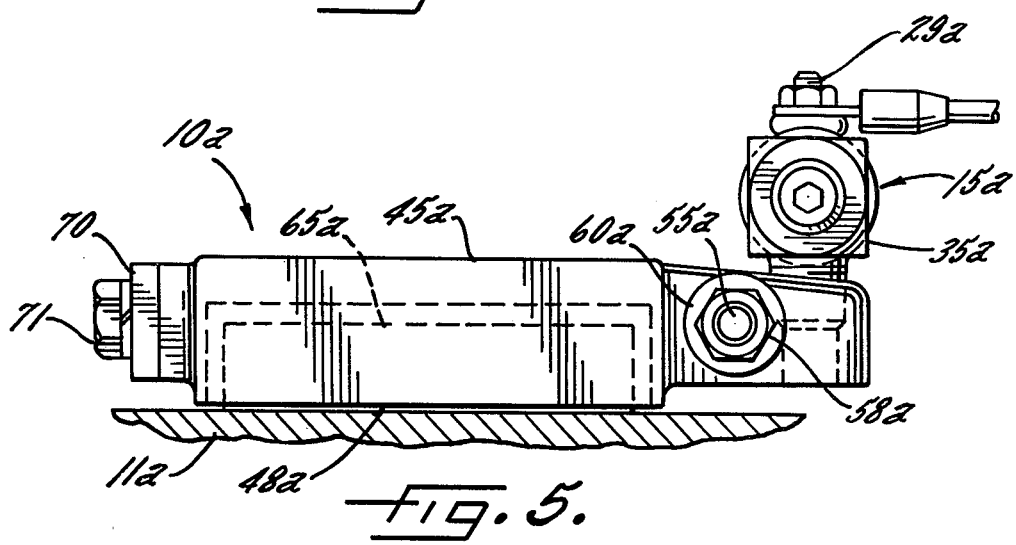
FIG. 5 is a side view of the strain sensing device shown in FIG. 4.

Referring now to FIGS. 4 and 5, there is shown an alternative form of strain sensing device embodying the present invention, wherein similar elements have been given the same reference numeral with the distinguishing suffix "a" added. The strain sensing device 10a again includes a pair of elongated mounting blocks 45a each including a magnetic element 65a. In this instance, only one end of the mounting blocks 45a have lugs 50a flexibly coupled by a connecting rod 55a. The lugs 50a in this case also carry the transducer support brackets, which threadably engage the lugs. For more rigidly coupling the opposite ends of the mounting blocks 45a, a plastic plate 70 is secured between the ends of the blocks by screws 71. Although the plastic plate provides a more rigid coupling between the ends of the mounting blocks, because of the relatively high Youngs Modulus for plastic, it nevertheless has sufficient yielding characteristics to permit transmission of forces from the mounting blocks to the transducer. The strain sensing device 10a can be used in the same manner already described.

From the foregoing, it can be seen that the strain sensing device of the present invention can be readily mounted and repositioned on various force carrying members of production machinery for purposes of demonstrating load monitoring systems as well as locating specific locations on such force carrying members that are exposed to maximum stress concentrations. The strain sensing device is easy to use, simple in construction, and lends itself to economical manufacture.

We claim our invention as follows:

1. A device for sensing deformation on a metal force carrying member comprising a strain sensing element, means operatively mounting said strain sensing element on said force carrying member, said mounting means including magnetic element means which permit said device to be secured on said force carrying member by means of magnetic attraction forces between said magnetic element means and said force carrying member as an incident to positioning of said mounting means on said member, and said magnetic element means having sufficient magnetic strength for enabling strain in said force carrying member to be transmitted through said mounting means to said strain sensing element while permitting selected manual removal and repositioning of said device on said force carrying member.

2. The device of claim 1 in which said mounting means includes a pair of brackets between which said transducer is interposed, and said brackets each have magnetic mounts for removably securing said brackets on said machine member so as to transmit changes in strain deformation from said member to said sensing element.

3. The device of claim 2 including means coupling said magnetic mounts for guiding relative movement of said mounts during changes in strain deformation of said member.

4. The device of claim 2 in which said magnetic mounts each have a holding power of between about 40 and 50 pounds.

5. A device for sensing deformation on a force carrying member comprising a transducer for generating an electrical output signal proportional to the applied loading, a pair of brackets supporting said transducer in a line parallel with the strain to be detected, means for removably mounting said brackets on said force carrying member, said mounting means for each bracket including a magnetic element for securing said bracket in place on said member by magnetic attraction between said magnetic element and said force carrying member, and said magnetic element having sufficient magnetic strength for enabling strain in said force carrying member to be transmitted through said brackets to said transducer while permitting selected manual removal and repositioning of said device on said force carrying member.

6. The device of claim 5 in which said mounting means includes a pair of spaced mounting blocks, said mounting blocks each carrying a respective one of said brackets, flexible connecting means coupled between said mounting blocks for maintaining the spacing between said blocks such that said transducer is retained between said brackets while permitting limited relative movement of said blocks and the bracket mounted thereon as an incident to deformation of the force carrying member upon which said device is mounted.

7. The device of claim 6 in which said mounting blocks are formed with aligned apertures, said connecting means including a rod which passes through said aligned apertures, and means coupling said mounting blocks to said rod for limited relative movement.

8. The device of claim 5 in which said mounting blocks each have an elongated configuration and are disposed in spaced parallel relation with said transducer extending between and transversely of said mounting blocks.

9. The device of claim 8 in which said transducer extends across the center of said mounting blocks, and means flexibly coupling together corresponding adjacent ends of said mounting blocks so as to retain said transducer between said brackets while permitting said mounting blocks and the brackets carried thereby to experience limited relative movement in a direction parallel to said transducer as an incident to deformation of said force carrying member.

10. The device of claim 8 in which said transducer is coupled between adjacent ends of said mounting blocks.

11. The device of claim 5 in which said magnetic element for each mounting means has a holding power of between 40 and 50 pounds.

12. The device of claim 5 in which said transducer includes a piezoelectric crystal and a pair of terminals electrically coupled to opposed faces of said crystal.

13. The device of claim 5 in which said transducer includes a pair of terminal blocks and a piezoelectric crystal interposed therebetween, said terminal blocks and crystal being supported between said brackets in a line parallel to the stress to be detected.

* * * * *